(12) United States Patent
Engelmann et al.

(10) Patent No.: US 6,303,399 B1
(45) Date of Patent: Oct. 16, 2001

(54) METHOD OF SAMPLE PREPARATION FOR ELECTRON MICROSCOPY

(75) Inventors: Hans-Juergen Engelmann, Dresden; Beate Volkmann, Freiberg; Ehrenfried Zschech, Moritzburg, all of (DE)

(73) Assignee: Advanced Micro Devices Inc., Austin, TX (US)

( * ) Notice: Subject to any disclaimer, the term of this patent is extended or adjusted under 35 U.S.C. 154(b) by 0 days.

(21) Appl. No.: 09/800,441

(22) Filed: Mar. 6, 2001

(30) Foreign Application Priority Data

Sep. 12, 2000 (DE) ............................. 100 45 041

(51) Int. Cl.⁷ .................................................. H01L 21/66
(52) U.S. Cl. ................... 438/14; 438/12; 438/15; 438/16; 438/17
(58) Field of Search ................... 438/14, 15, 16, 438/17, 12

(56) References Cited

U.S. PATENT DOCUMENTS

| | | | | |
|---|---|---|---|---|
| 4,711,822 | * | 12/1987 | Choyke et al. | 428/458 |
| 5,767,516 | * | 6/1998 | Kawanami et al. | 250/311 |
| 5,936,237 | * | 8/1999 | van der Weide | 250/234 |
| 6,112,004 | * | 8/2000 | Colvin | 385/116 |
| 6,134,365 | * | 10/2000 | Colvin | 385/116 |
| 6,245,586 | * | 6/2001 | Colvin | 438/15 |

* cited by examiner

Primary Examiner—John F. Niebling
Assistant Examiner—Olivia Luk
(74) Attorney, Agent, or Firm—Williams, Morgan & Amerson

(57) ABSTRACT

A method is provided for preparing a sample for cross-section analysis by a transmission electron microscope. Semiconductor samples containing recessed portions or unfilled structures are filled with a filling material so as to produce a planar top surface onto which a metal layer can be deposited for thinning the sample to a thickness of less than 100 nm by an FIB technique.

23 Claims, 1 Drawing Sheet and ana-# METHOD OF SAMPLE PREPARATION FOR ELECTRON MICROSCOPY

BACKGROUND OF THE INVENTION

1. Field of the Invention

The present invention relates to sample analysis by means of charged particle beams, and, in particular, to sample preparation for electron microscope analysis of semiconductor devices.

2. Description of the Related Art

The manufacturing process of integrated circuits involves the fabrication of numerous semiconductor elements such as insulated gate field-effect transistors or metal-oxide semiconductor field-effect transistors (MOSFETs) within a small chip area. In order to increase integration density and improve device performance, for instance, with respect to signal processing time and power consumption, feature sizes of the transistor structures are steadily decreasing. At the same time, economic constraints require a high yield and throughput in manufacturing the semiconductor devices, while, on the other hand, high quality and reliability of the end products are of great importance. Accordingly, a modern process flow for fabricating cutting-edge semiconductor devices implements a plurality of methodologies and analyzing methods to guarantee product quality.

Important ways of analyzing material properties, as well as structural characteristics of the semiconductor device, during various manufacturing stages, include those physical methods that allow ions, electrons, and/or electromagnetic radiation to interact with matter and then examine the secondary particles and/or radiations that are produced. The information obtained from the interaction of the particles and/or radiation with a region of interest in the semiconductor device is then used to deduce the properties of the materials in the region of interest.

Typical instruments widely used in the field of semiconductor manufacturing are electron microscopes, which may be classified into Scanning Electron Microscopes (SEM), Transmission Electron Microscopes (TEM), and Auger Electron Spectrometers (AES). The TEM analysis is steadily gaining importance, in particular, since transmission of electrons through a sample allows, in addition to obtaining information via localized atomic properties, obtaining information via diffraction mechanisms, which, in turn, provide information concerning longer-range order. Unfortunately, sample preparation for TEM analysis is difficult and time-consuming, since the thickness of the sample must not exceed about 100 nm to yield meaningful results.

To prepare cross-sectional samples having the required small thickness of 100 mn and less, several techniques have been used in the prior art. A typical method includes grinding, dimpling, and Ar$^+$-ion milling of the sample. This technique, however, is very time-consuming and, therefore, not suited for rapidly gathering information regarding the manufacturing process. Furthermore, it is difficult to determine the local position of the cross-section with respect to the device structure being investigated.

A further preparation technique includes the cutting and thinning of samples by means of a focused ion beam (FIB), which, in general, allows relatively fast sample preparation, and has, therefore, become the preferred method of sample preparation for TEM analysis. Moreover, this method allows a lateral orientation on the sample so that the cross-section can be prepared in a selected area, at least within certain boundaries, of the portion of the semiconductor device to be analyzed. In a typical preparation process including the FIB technique, a sample has initially been cut and thinned to provide a sample having opposing side surfaces that represent a cross-section of a device structure to be investigated. The thinning process is carried out until a cross-sectional thickness, i.e., a distance between the two opposing side surfaces, has been reduced to a thickness of about 30 to 50 μm. Then, a metal layer has to be deposited on the top surface of the sample forming a cutting line for the subsequent focused ion beam operation. The metal layer, preferably consisting of Pt or W, may be deposited by any appropriate deposition method or, preferably, by means of the FIB apparatus using a low beam intensity. The sample having the metal layer as a cutting line on its top surface is then exposed to the high intensity focused ion beam that orthogonally impinges the metal layer. By scanning the focused ion beam across the top surface, sample material is continuously removed, thereby gradually reducing the cross-sectional thickness of the sample until the final thickness required for TEM analysis is obtained.

The preparation process described above, however, requires a planar top surface for depositing the metal layer as the cutting line without any defects to achieve appropriately formed side surfaces suitable for the transmitting electron beam of the TEM.

Due to the ever-decreasing device features, however, investigation of device structures containing openings, such as via chains and trenches that have to be filled by a dual damascene process or local interconnects, is required in fabricating high quality devices. These structures, however, do not have a planar top surface, and, when subjected to the FIB process, thus result in poor cross-section samples for TEM analysis. As a consequence, sample preparation for TEM analysis of openings in a semiconductor structure has been difficult and time-consuming and, thus, a cost-intensive procedure.

In view of the above, there exists a need for an improved method of preparing a sample for cross-sectional analysis, providing high yield and samples of high quality.

SUMMARY OF THE INVENTION

According to one aspect of the present invention, a method of preparing a sample of a semiconductor device for electron microscopy is provided, the method comprising providing the sample having a surface and including a recessed portion formed in the surface, applying a liquid curable filling material to the surface of the sample, and exposing the sample to an ambient of low pressure, removing residual air and gas from the recessed portion and allowing the liquid curable filling material to penetrate the recessed portion. The method also comprises increasing the pressure of the ambient to support penetration of the recessed portion by the liquid curable filling material, the ambient of increased pressure enabling substantially complete filling of the recessed portion, removing residual filling material from the surface of the sample, and curing the liquid curable filling material by performing a heat treatment, converting the filling material to a solid phase and planarizing the surface. The method additionally comprises depositing a metal layer on the planarized surface to provide a cutting line for a focused ion beam (FIB) treatment of the sample for cutting the sample to dimensions required for cross-section analysis.

According to a further aspect of the present invention, a method of preparing a semiconductor sample for transmission electron microscope analysis is provided, the method comprising cutting and polishing a semiconductor wafer to obtain the semiconductor sample, the semiconductor sample including a region of interest having a top surface and two opposing side surfaces and a plurality of openings formed in the top surface, filling the openings by supplying a liquid curable filling material to the top surface, and wiping the top surface to remove residual filling material and planarize the top surface. The method also comprises curing the filling material, depositing a metal layer on the top surface to define a cutting line, and directing a focused ion beam (FIB) onto the top surface for removing material in the region of interest, at least in a portion thereof, to reduce a distance between the two side surfaces, until the distance is suitable for transmission electron microscopy.

According to still another aspect, a method of preparing a semiconductor sample for electron microscope analysis is provided, the method comprising the steps of: providing a semiconductor structure having a patterned top surface, providing a liquid curable filling material having a viscosity depending on at least one parameter, and exposing the semiconductor structure to a low pressure ambient to remove gas from the top surface. The method also comprises applying the liquid curable filling material to the patterned top surface, lowering the viscosity of the filling material by changing the parameter value to allow the filling material to substantially uniformly cover at least a portion of the patterned top surface, and curing the filling material to convert the filling material to a solid phase. The method additionally comprises depositing a metal layer at least over a sub-portion of the covered portion, and directing a focused ion beam (FIB) onto the sub-portion to remove material from the semiconductor sample so as to form two opposing side surfaces substantially perpendicular to the top surface, the two opposing side surfaces having a final distance of about 100 nm or less.

The present invention allows the filling of a recessed portion and/or a patterned top surface, which may include openings such as via chains and/or trenches for local interconnects of a semiconductor device in an intermediate stage, with a liquid filling material, without a complex deposition step, and further allows the planarizing of the top surface of the structure to be thinned by means of an FIB process. The procedure of filling the recessed portion includes removing of any residual air and/or gas by applying a vacuum to the sample, wherein prior to, and/or during, the application of vacuum the liquid filling material is applied to the top surface of the sample. According to one aspect, the viscosity of the liquid curable filling material, which depends on a parameter such as the temperature of the filling material, may be decreased by changing the parameter so as to uniformly distribute the filling material over a portion of the top surface to planarize the top surface. According to another aspect, the filling material is forced to completely fill the recessed portion substantially without any voids with a subsequent pressurizing step. By removing the residual filling material, for example, by wiping, a planar top surface is formed. Removing the residual filling material may be carried out in such a manner that a layer of filling material is formed on the entire top surface of the sample. The layer of filling material allows a further polishing step after curing the filling material so as to further improve the smoothness of the top surface for the subsequent metal deposition process.

BRIEF DESCRIPTION OF THE DRAWINGS

Further advantages and objects of the present invention will become more apparent with the following detailed description when considered in reference to the accompanying drawings in which.

DETAILED DESCRIPTION OF THE INVENTION

Figure 1A:
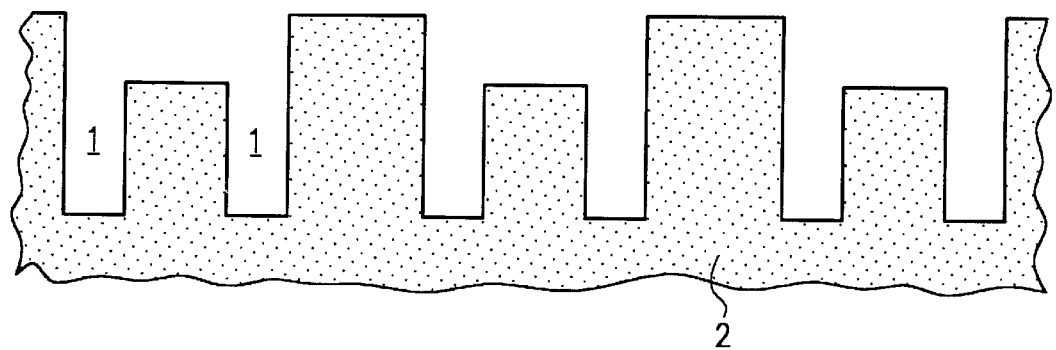
FIG. 1a is a schematic cross-sectional side view of a portion of a semiconductor structure including an unfilled via chain that is to be analyzed for step coverage of a barrier layer

While the present invention is described with reference to the embodiments as illustrated in the following detailed description as well as in the drawings, it should be understood that the following detailed description as well as the drawings are not intended to limit the present invention to any particular embodiment disclosed, but rather, the described embodiment merely exemplifies the various aspects of the present invention, the scope of which is defined by the appended claims.

FIG. 1a schematically shows a cross-sectional view of a portion of a semiconductor device in an intermediate manufacturing stage. In the bulk material of a substrate 2, a plurality of vias 1 are formed. The substrate 2 may be comprised of any appropriate material such as silicon, germanium, and the like, having additional material layers formed thereon in conformity with design requirements. Underlying layers, however, are not shown for the sake of simplicity. Furthermore, the vias 1 are only representative of an arbitrarily recessed portion in the substrate 2. The method of the present invention may be applied to any surface structure including a recessed portion or any type of unfilled structure.

As previously noted, ever decreasing device features require accurate control of the various manufacturing steps, such as depositing a thin barrier layer on the surface of the vias 1, to monitor, for example, the step coverage of the deposition process. To this end, TEM analysis of the cross-section schematically depicted in FIG. 1a is an adequate way to gather the desired information. Since TEM analysis requires a sample thickness of about 100 nm at most, the semiconductor has to be cut and thinned so as to provide a cross-sectional area having the required sample thickness.

Figure 1B:
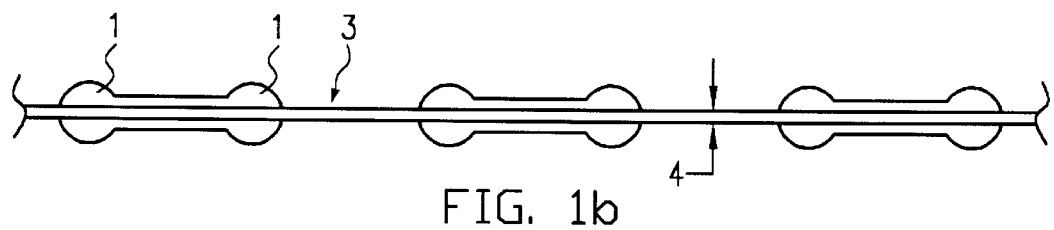
FIG. 1b is schematic top view of the portion of the unfilled via chain of FIG. 1a, wherein a thickness of the TEM cross-section to be prepared is indicated.

FIG. 1b schematically shows a top view of the via chain structure depicted in FIG. 1a. Reference numeral 3 represents the cross-section area required for the TEM analysis, where a thickness 4 of the cross-section area is less than about 100 nm.

Since a relatively fast and efficient method of sample preparation is necessary, FIB cutting of the sample, which has already been thinned to a thickness of a few 10 $\mu$m by any appropriate method well-known to the skilled person, is the preferred technique. FIB cutting allows precise adjustment of the ion beam and precision scanning of the ion beam over the surface of the sample so as to selectively remove the sample material adjacent to area 3.

Figure 2:
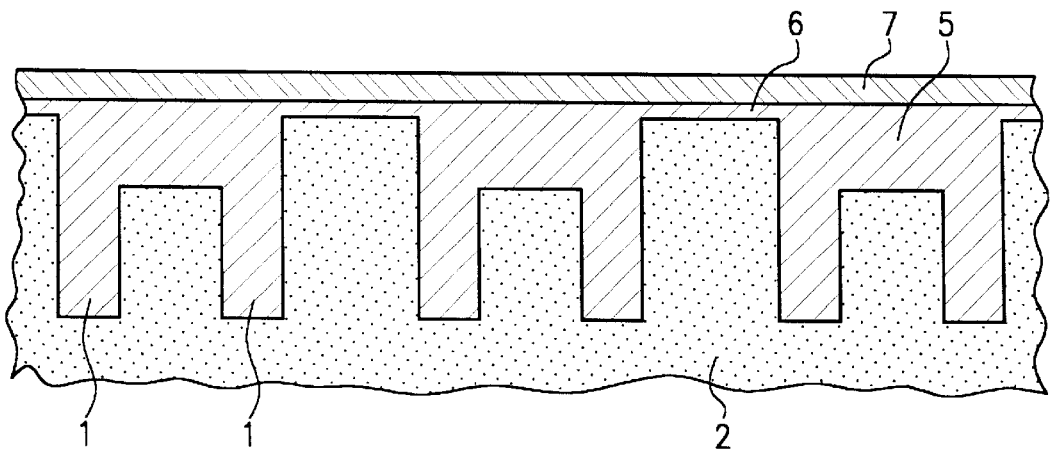
FIG. 2 is a schematic cross-sectional side view of the via chain structure of FIG. 1, wherein the vias have been filled according to one illustrative embodiment of the present invention.

FIG. 2 schematically shows the cross-section of area 3 depicted in FIG. 1b in a plane view after the method in accordance with an embodiment of the present invention has been carried out. The vias 1 are filled with a filling material 5, which also forms a fill layer 6 on top of the substrate 2. A metal layer 7 is formed on the fill layer 6.

The cross-sectional area 3 illustrated in FIG. 1b may be obtained by the following process flow. The cross-sectional area 3, already thinned to a few 10 µm, is mounted on an appropriate support. Hereinafter, the surface representing a portion of the sample depicted in the top view of FIG. 1b is referred to as top surface, whereas the surfaces formed by thinning the sample in a direction perpendicular to the top surface and schematically depicted in FIGS. 1a and 2 are referred to as side surfaces. The liquid curable filling material 5 is supplied to the top surface of the sample, for example as a drop having a volume sufficient to completely fill the vias 1. The filling material may be an epoxy material, for example, M-Bond 610™. Next, the sample is introduced into a vacuum chamber adequately equipped to produce a prevacuum to remove air and other gases from the vias 1. In order to avoid penetration of the vias 1 by the liquid filling material 5 and sealing of the vias 1 prior to removing air and gas from the vias 1, advantageously the liquid filling material 5 may be provided to the sample within the vacuum chamber after applying reduced pressure to the sample. For removing air and gas from the vias 1, only a short time period of pre-vacuum in a range of about 0.5 to about 10 seconds is sufficient. Thereafter, filling the vias 1 with the liquid filling material 5 is enhanced by applying pressure to the sample, preferably by ventilating the vacuum chamber. The resulting pressure acting upon the liquid filling material 5 is thus dependent on the amount of ventilation, which is controllable, for example, by a flow restrictor in the ventilation pipe. The pressure may be adjusted to any desired value from pre-vacuum to atmospheric pressure. When the vacuum chamber is connected to a source of pressurized gas, a pressure exceeding atmospheric pressure can be used to accelerate the filling process. Depending on the dimensions of the recessed portion, for example, the vias 1, and depending on the viscosity of the filling material 5, the pressure is adjusted to obtain substantially completely filled vias.

In order to further improve the act of filling the vias 1, it may be advantageous to heat the sample for a short time period to reduce the viscosity of the liquid filling material 5 without initiating hardening of the filling material 5. Reducing the viscosity is particularly advantageous when the surface structure includes openings having a large aspect ratio, for example, large depth and small diameter, since otherwise the openings may not be filled completely, resulting in a non-planar top surface that substantially resembles the surface shape of the unfilled openings.

Next, residual filling material is removed from the top surface of cross-sectional area 3 by, for example, wiping the surface. As shown in FIG. 2, the thin fill layer 6 may be formed on the top surface of area 3. Thereafter, the filling material is cured by heating the sample. This can be accomplished by any appropriate means such as an oven, or a heater, preferably provided in the vacuum chamber, and the like Then, the metal layer 7, for example, a Pt layer or a W layer, is deposited over the fill layer 6. For deposition of the metal layer 7, any suitable process including deposition with an FIB apparatus may be employed. Prior to depositing metal layer 7, a further polishing step may be performed to enhance the smoothness of fill layer 6 and/or to completely remove fill layer 6.

Due to the filling of the vias 1, a smooth and planar top surface is provided and thinning of the cross-sectional area 3 to the required thickness 4 can be performed by an FIB technique, as previously described. In the present example, a $Ga^+$ ion beam is used to cut the sample. The $Ga^+$ ion beam also removes the filling material without any disadvantageous effects to the sample. Finally, the cross-sectional area 3 is obtained having side surfaces which are spaced apart from each other by a distance of less than 100 nm. The cross-sectional area thus prepared is suitable for TEM analysis.

In a further embodiment, the liquid curable filling material is applied to the top surface of the sample while the sample is exposed to a low pressure ambient. Next, the viscosity of the filling material is decreased by changing a parameter affecting the viscosity of the filling material, such as the temperature of the filling material, to allow the low-viscosity filling material to substantially uniformly fill a recessed portion in the top surface. The further processing of the filling material, for example, wiping, curing, and the like, may be performed as described above.

It should be noted that, according to the present invention, samples already prepared for cross-section analysis by SEM may also additionally be prepared for TEM analysis. Moreover, the present invention allows the preparation of any unfilled semiconductor device structure for TEM analysis, thereby insuring a high efficiency and reliability with a yield of nearly 100%.

It will be appreciated that modifications to the above process flow may be made without departing from the scope of the present invention. For example, the liquid curable filling material 5 may be applied to the top surface of the semiconductor device prior to the initial thinning of the sample to a few µm. In this case, the sample handling involved with applying and curing the filling material (transport, heating, polishing) can be performed by the standard wafer handling equipment, rather than handling a single wafer piece including the sample. Moreover, application of the liquid filling material may be performed in a way similar to the application of photoresist onto a wafer.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the present invention. It is to be understood that the forms of the invention shown and described herein are to be taken as the presently preferred embodiments. Elements and materials may be substituted for those illustrated and described herein.

What is claimed:

1. A method of preparing a sample of a semiconductor device for electron microscopy, the method comprising:

providing the sample having a surface and including a recessed portion formed in the surface;

applying a liquid curable filling material to the surface of the sample;

exposing the sample to an ambient of low pressure, removing residual air and gas from the recessed portion and allowing the liquid curable filling material to penetrate the recessed portion;

increasing the pressure of the ambient to support penetration of the recessed portion by the liquid curable filling material, the ambient of increased pressure enabling substantially complete filling of the recessed portion;

removing residual filling material from the surface of the sample;

curing the liquid curable filling material by performing a heat treatment, converting the filling material to a solid phase and planarizing the surface; and depositing a metal layer on the planarized surface to provide a cutting line for a focused ion beam treatment of the sample for cutting the sample to dimensions required for electron microscopy.

2. The method of claim 1, wherein the liquid curable filling material is an epoxy material.

3. The method of claim 1, wherein the recessed portion in the sample includes one or more openings, the openings having a depth and a diameter in a range of about 0.1 $\mu$m to about 5 $\mu$pm.

4. The method of claim 1, wherein removing residual filling material includes wiping the sample surface so as to planarize the sample surface.

5. The method of claim 1, wherein removing residual filling material includes forming a layer of filling material over the sample surface, the layer of filling material having a planar surface.

6. The method of claim 5, further comprising polishing the planar layer of filling material after curing the filling material, improving smoothness of the planar surface.

7. The method of claim 1, further comprising: inserting the sample into a pre-vacuum chamber, applying the low pressure for a time period in a range of about 0.5 seconds to about 10 seconds, and pressurizing the sample in the pre-vacuum chamber by introducing gas.

8. The method of claim 7, wherein pressurizing is performed by ventilating the pre-vacuum chamber.

9. The method of claim 7, wherein a pressure for pressurizing the sample is in a range of about 0.1 atm to 5 atm.

10. The method of claim 1, wherein the sample is a semiconductor sample prepared for scanning electron microscope analysis.

11. The method of claim 1, wherein the liquid curable filling material is applied as a drop prior to exposing the sample to the low pressure ambient.

12. The method of claim 1, wherein the liquid curable filling material is applied as a drop during exposure of the sample to the low pressure ambient and prior to pressurizing the sample.

13. A method of preparing a semiconductor sample for transmission electron microscope analysis, the method comprising:

cutting and polishing a semiconductor wafer to obtain the semiconductor sample, the semiconductor sample including a region of interest having a top surface and two opposing side surfaces and a plurality of openings formed in the top surface;

filling the openings by supplying a liquid curable filling material to the top surface;

wiping the top surface to remove residual filling material and planarize the top surface;

curing the filling material;

depositing a metal layer on the top surface to define a cutting line;

directing a focused ion beam onto the top surface for removing material in the region of interest, at least in a portion thereof, to reduce a distance between the two side surfaces, until the distance is suitable for transmission electron microscopy.

14. The method of claim 13, wherein filling the openings comprises supplying the liquid curable filling material to the top surface, wherein at least portions of the openings remain exposed;

exposing the region of interest to a low pressure ambient, allowing the liquid filling material to penetrate the openings; and pressurizing the region of interest to force the liquid filling material into the openings to substantially completely fill the openings.

15. The method of claim 13, wherein at least one of the side surfaces forms a cross-section of the openings when the distance is less than about 100 nm.

16. The method of claim 13, wherein the focused ion beam includes $Ga^+$ ions.

17. The method of claim 13, wherein the filling material is an epoxy material.

18. The method of claim 14, wherein the filling material is applied to the top surface while the region of interest is exposed to the low pressure ambient.

19. The method of claim 13, wherein a time period of exposing the region of interest to the low pressure ambient is in a range of about 0.5 to 10 seconds.

20. The method of claim 13, wherein the region of interest is pressurized after exposure to the low pressure ambient by exposing the region of interest to atmospheric pressure.

21. The method of claim 13, wherein the distance is less than about 100 nm.

22. The method of claim 13, wherein the semiconductor sample is a semiconductor sample prepared for scanning electron microscopy.

23. A method of preparing a semiconductor sample for electron microscope analysis, the method comprising:

providing a semiconductor structure having a patterned top surface;

providing a liquid curable filling material having a viscosity depending on at least one parameter;

exposing the semiconductor structure to a low pressure ambient to remove gas from the top surface;

applying the liquid curable filling material to the patterned top surface;

lowering the viscosity of the filling material by changing the parameter value to allow the filling material to substantially uniformly cover at least a portion of the patterned top surface;

curing the filling material to convert the filling material to a solid phase;

depositing a metal layer at least over a sub-portion of the covered portion; and directing a focused ion beam onto the sub-portion to remove material from the semiconductor sample so as to form two opposing side surfaces substantially perpendicular to the top surface, the two opposing side surfaces having a final distance therebetween of about 100 nm or less.

* * * * *